United States Patent [19]

Smigocki et al.

[11] Patent Number: 5,792,934
[45] Date of Patent: *Aug. 11, 1998

[54] ENHANCED INSECT RESISTANCE IN PLANTS GENETICALLY ENGINEERED WITH A PLANT HORMONE GENE INVOLVED IN CYTOKININ BIOSYNTHESIS

[75] Inventors: Ann C. Smigocki, Silver Spring; John W. Neal, Jr., Laurel, both of Md.

[73] Assignee: The United States of America as represented by the Secretary of Agriculture, Washington, D.C.

[*] Notice: The term of this patent shall not extend beyond the expiration date of Pat. No. 5,496,732.

[21] Appl. No.: 609,320

[22] Filed: Mar. 1, 1996

Related U.S. Application Data

[63] Continuation of Ser. No. 54,985, Apr. 30, 1993, Pat. No. 5,496,732.

[51] Int. Cl.⁶ ............... C12N 15/29; C12N 15/00; C12N 15/82; A01H 5/00
[52] U.S. Cl. ............ 800/205; 435/320.1; 435/70.1; 435/172.3; 536/23.2; 536/23.6; 536/23.7; 536/24.1
[58] Field of Search ............. 800/205; 435/320.1, 435/70.1, 172.3; 536/23.2, 23.6, 23.7, 24.1

[56] References Cited

PUBLICATIONS

Gatehouse, et al., *Advanced Methods in Plant Breeding and Biotechnology*, pp. 250–276 (1991).
Nicholson, R.L., *Annu. Rev. Phytopathol.*, vol. 30, pp. 369–389 (1992).
Bailiss, et al., *Ann. Appl. Biol.*, vol. 87, pp. 383–392 (1977).
Balazs et al., *Phytopathology*, vol. 100, pp. 356–360 (1981).
Memelink et al., *EMBO J*, vol. 6, pp. 3579–3583 (1987).
Chen et al., *EMBO J*, vol. 4, pp. 2145–2151 (1985).
Ward et al., *The Plant Cell*, vol. 3, pp. 1085–1094 (1991).
Hallahan et al., *Plant Genetic Manipulation for Crop Protection*, pp. 212–248 (1992).
Hedin et al., *J. Agri. Food Chem.*, vol. 36, pp. 746–748 (1988).
Thomas et al., *Monograph British Growth Regulator Group*, vol. 14, pp. 69–83 (1987).
Teutonico et al, *Plant Physiol.*, vol. 97, pp. 288–297 (1991).
Gatehouse et al., *Plant Genetic Manipulation for Crop Protection*, pp. 155–181 (1992).
Van Larebeke et al., *Nature*, vol. 252, pp. 169–170 (1974).
Barker et al., *Plant Molecular Biology*, vol. 2, pp. 335–350 (1983).
Smigocki et al., *Plant Molecular Biology*, vol. 16, pp. 105–115 (1991).
Smigocki et al., *Proc. Natl. Acad. Sci*, vol. 85, pp. 5131–5135 (1988).
Thornburg et al., *Proc. Natl. Acad. Sci*, vol. 84, pp. 744–748 (1987).

*Primary Examiner*—Douglas W. Robinson
*Assistant Examiner*—Thomas Haas
*Attorney, Agent, or Firm*—M. Howard Silverstein; John Fado; Janelle S. Graeter

[57] ABSTRACT

A transgenic plant into which a chimeric gene comprising a wound inducible promoter and a gene for an enzyme involved in cytokinin biosynthesis has been introduced shows enhanced resistance to insect infestation.

4 Claims, 11 Drawing Sheets

GATCTTTGAAATTAGACAAGTATTATCGGACATCTCTACTTTTAGTATAGTAAACAAGTAAAGATCGATAAAGAGAGTAAT
TACCTTGCCAAATAATTAACTAACAAGCACACATCTTTTTTTTATCAAATATTAATAAAAATAATTTATATTAATATGA
TGCTATCTTTTGATCACTCGTTTGCTATAAATAGGTGGAGGAGGACAGACACTCTTCACCCCAAATTAAAAGAAAAAG

FIG. 1

```
ATGGACCTGCATCTAATTTTCGGTCAAACTTGCACAGGAAAGACGACGACCGCGATAGCTCTTGCCCAGCAGACAGGGCT
GGGTCCAATGCTGTCCCTCAACTATCAACCGGAAGCGGACGACCAACAGTGGAAGAACTGAAAGGAACGACCGTCTCTAC
GGAGGGTATCATCGCCAGCCAAGCTCATCATAGGCTGATCGAGGAGGTGTATAATCATGAGGCCAACGGCGGGCTTA
TCGTTGCTCAACTGCATGGGCGGAAAGAGCTATTGGAGTGCAGATTTTCGTTGGCATATTATTCGCCACAAGTTACCCGA
CGGCCAAGGCCAGAGTTAAGCCAGATGTTGCACCCCCCTGCAGGCCATTCTATTATTCAGAGTTGGTTTATCTTTGGAAT
TTCTGAAAGAGATCGATGGATATCGATATGCCATGTTGTTTGCTAGCCAGCCAACAGGGACAGAAATTCCCCCAAGTTAACGCAG
TAAGTTGATTAATGGGATCGCTCAGGAGTATTTCATCCATGCCGCC
GGTCATCCGTTCGGAATGTATTAG
```

FIG. 2A

GATAACCACAATTCTCTAATATAAAAAATCAGTTTGTATTCAATATACTGCAAAAAACTTATG

FIG. 2B

ENHANCED INSECT RESISTANCE IN PLANTS GENETICALLY ENGINEERED WITH A PLANT HORMONE GENE INVOLVED IN CYTOKININ BIOSYNTHESIS

This is a continuation of application Ser. No. 08/054,985 filed Apr. 30, 1993, now U.S. Pat. No. 5,496,732.

BACKGROUND OF THE INVENTION

1. Field of the Invention

One of the most important constraints on the yields of food and cash crops worldwide can be attributed to insect attack. Based on 1987 figures approximately 37% of all crops produced worldwide are lost to pests such as insects (13%), disease (12%), and weeds and grasses (12%). Annually, large sums of money are spent on chemical pesticides to reduce these levels of crop damage. In 1987 the insecticide expenditures for the three crops receiving the highest insecticide input—cotton, maize and rice—was almost $4000 million. Approximately $3000 million was spent on purchasing the insecticide and $1000 million for application. In the U.S. alone, over $400 million is spent each year for control of lepidopterans.

Dependance on chemical pesticides for crop damage control is not only expensive, but it is also detrimental to the environment and unhealthy for the animal population. Many chemical insecticides, particularly organophosphates and carbamates, are neurotoxic to a wide range of animals from honey bees to humans. A number of them have been discontinued because of their toxic properties. Thus, scientists are currently seeking alternatives to the conventional chemical approach to crop pest management, and one approach is the investigation of plant-mediated, and thus more environmentally friendly, methods and products.

Scientists have long used cross-breeding and hybridization techniques to provide plants having particular desired traits such as increased hardiness, nutritional value, taste, appearance, etc., but these techniques are at best lengthy, time-consuming processes which do not necessarily result in the achievement of a particular goal. The advent of genetic engineering, however, provided the opportunity to introduce genetic material directly into a plant, which, upon expression in the plant, would result in a desired effect.

DESCRIPTION OF THE PRIOR ART

A limited number of insect-control agents are currently available for genetic engineering into plants. The protein delta endotoxins from the microorganism *Bacillus thuringiensis* (Bt) have been the most widely studied in transformed plants, and the class of proteins known as proteinase inhibitors, when present at relatively high levels in the diet, has been shown to be effective against certain insects. The potential disadvantages to using transgenic Bt plants are that effective concentrations may be difficult to achieve in the plant and that insect resistance may develop with time. The high levels of protein required for insect killing and the potential need to target protein expression to specific plant organs are problems associated with usage of proteinase inhibitors as insect-control agents.

Phytohormones are known to have pivotal roles in promoting normal growth and development of plants and may also contribute to the mechanisms of defense (Gatehouse, 1991; Nicholson, 1992). Cytokinins are among the most active plant substances discovered and have been implicated in the physiological and biochemical processes with marked effects on flowering, fruit set and ripening, leaf senescence, seed germination and stomatal function. Exogenously applied cytokinins have been shown to suppress the induction of hypersensitive necrosis by viruses (Bailiss et al., 1977; Balazs and Kiraly, 1981). High endogenous cytokinin levels in non-rooting tobacco shoot lines (T-cyt) transformed with a gene involved in cytokinin biosynthesis caused an increase in the expression of defense-related mRNAs (Memelink et al., 1987). A group of pathogenesis related proteins encoded by these genes is coordinately induced by wounding and pathogenic infections (Chen and Varner, 1985; Ward et al., 1991).

Cytokinins as well as other plant hormones have commercial applications as bioregulators and, in combination with endogenous hormones, may protect plants from pests and pathogens by inducing physiological changes in the plants (Hallahan et al., 1991; Hedin et al., 1988; Thomas and Balkesley, 1987).

Cytokinins have also been shown to influence secondary metabolic pathways whose products exhibit insecticidal properties (Teutonico et al., 1991). Utilization of numerous secondary metabolites in crop protection, either by conventional plant breeding or by genetic engineering, is currently being evaluated (Gatehouse et al., 1992; Hallahan, supra).

Thus, although phytohormones, and cytokinins in particular, have been implicated in conferring resistance to insects in plants, the role of cytokinins in such resistance has not heretofore been evaluated nor have any attempts been made to utilize endogenous cytokinins to confer increased resistance to insects in plants.

SUMMARY OF THE INVENTION

We have discovered that expression in plants of a bacterial gene encoding the first enzyme in the cytokinin biosynthetic pathway, isopentenyl transferase (ipt), reconstructed to allow for wound regulated expression in plants, confers enhanced resistance to insect attack. The ipt gene was fused to a promoter (control region) from a potato gene originally isolated from wounded tubers. Expression of the reconstructed gene was demonstrated in leaves of transgenic plants following mechanical wounding or insect feeding.

In accordance with this discovery, it is an object of the invention to provide a gene construct comprising a wound inducible promoter region and a DNA sequence encoding the enzyme isopentenyl transferase.

It is also an object of the invention to provide a transformation vector comprising the novel gene construct subcloned into a vector effective for introducing the gene construct into a plant.

It is another object of the invention to provide a transgenic plant having enhanced insect resistance, wherein the enhanced resistance is a result of expression of the novel gene construct.

Other objects and advantages will become readily apparent from the ensuing description.

BRIEF DESCRIPTION OF THE DRAWINGS

FIG. 1. Sequence of 3' end of promoter region of potato PI-IIK gene.

FIG. 2. (A) Sequence of ipt gene. (B) Sequence of 5' region of truncated gene.

DETAILED DESCRIPTION OF THE INVENTION

Current interests are focusing on the combined effects of natural defense mechanisms of plants and biotechnology for crop improvement. The role of cytokinins in insect resistance was therefore evaluated with respect to their influence on conferring enhanced insect resistance to plants susceptible to insect infestation.

In order to avoid uptake and metabolism associated with exogenous hormone applications, plants were genetically engineered with a wound-inducible cytokinin biosynthesis gene, the isopentenyl transferase (ipt) gene isolated from *Agrobacterium tumefaciens* (*A. tumefaciens*). While any effective wound-inducible promoter is acceptable, fusion of the ipt gene with a promoter from the potato proteinase inhibitor II (PI-II) gene known to be induced in the leaves of transgenic plants by mechanical wounding and/or insect chewing is preferred. The chimeric gene was introduced into plants for expression in tissues such as leaves.

The promoter was obtained from the 5' regulatory region of the potato PI-IIK gene (described by Thornburg et al., 1987, and herein incorporated by reference). A partial sequence from the 3' end of the promoter is shown in FIG. 1.

The gene was obtained from a library of potato genes using nick-translated tomato inhibitor II as a probe. A vector comprising regulatory regions, both promoter and terminator, of the wound-inducible gene fused to the open reading frame of the CAT gene was constructed and utilized to transform tobacco plants. Expression of the CAT gene in wounded tobacco leaves demonstrated the effectiveness of wound-inducible control on gene expression.

Fragments of the PI-IIK gene containing the promoter and terminator regions of the gene were inserted into the plasmid pUC13, resulting in plasmid pRT24. A 0.8 kb EcoRI/BamHI DNA fragment containing only the promoter region of the PI-IIK gene was then obtained from pRT24 for fusion with the ipt gene to form the gene construct.

The ipt gene was cloned from a tumor-inducing plasmid (pTiB6S3, described by van Larebeke et al., 1974, and Barker et al., 1983, both herein incorporated by reference) carried by *A. tumefaciens* as described by Smigocki, 1991, and Smigocki and Owens, 1988 (both herein incorporated by reference). The ipt gene sequence is shown in FIG. 2A. A 7.3 kb EcoRI fragment from the T-DNA region of pTiB6S3 was then cloned into pBR325. From that fragment, a 1.3 kb ipt-containing fragment was cloned into pUC18. The promoter region was removed with BAL-31 exonuclease, and the 5' region of the truncated gene was sequenced (see FIG. 2B). The sequence contains 723 nucleotides which code for a product of approximately 27 kd. The ipt gene sequence begins at position 8771 (ATG) and terminates at position 9493 (TAG) of the T-DNA gene (Barker, supra).

Figure 3A:
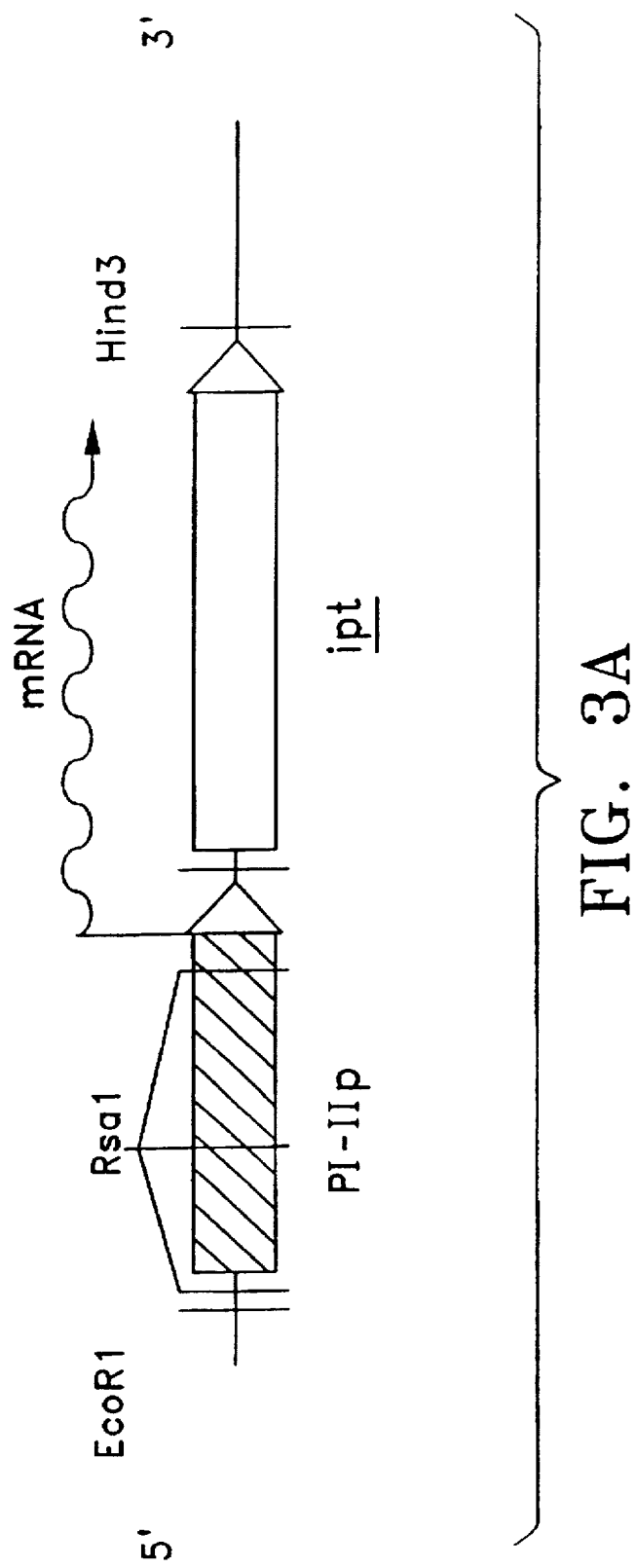
FIG. 3. (A) Chimeric PI-II-ipt gene construct. The potato proteinase inhibitor IIK gene promoter (PI-II$_p$) was fused through its 5'-untranslated region to the coding region of the isopentenyl transferase gene (ipt) from pTiB6S3. A transcription initiation site is located 101 bp upstream of the ipt gene start codon. (B) Binary Ti plasmid vector (pPICkn62). The vector contains the T-DNA right (TR) and left (TL) border sequences from pTiT37 for integration into the plant genome. The NPTII gene is used as a selectable marker for kanamycin-resistant plant cells. The tetracycline resistance gene (TC) allows selection in bacteria. Transcription terminator (rbcS3') is from the pea rbcS-E9 gene. (C) Analysis of ipt transcript levels in excised leaf disks at 6, 24, and 48 hours. Leaf disks were excised from fully expanded leaves on preflowering (PF) and flowering (F) homozygous PI-II-ipt plants (102, 108) and control plants. The 0 time corresponds to RNA from tissues collected immediately after excision.

The 0.8 kb fragment containing the PI-IIK promoter was fused by conventional means through its 5' untranslated region to the coding region of the truncated ipt gene (FIG. 3A). The truncated ipt gene carries its own transcription terminator and polyadenylation signals. Within the reconstructed gene, a transcription initiation site is located 101 bp upstream of the ipt gene start codon.

Figure 3B:
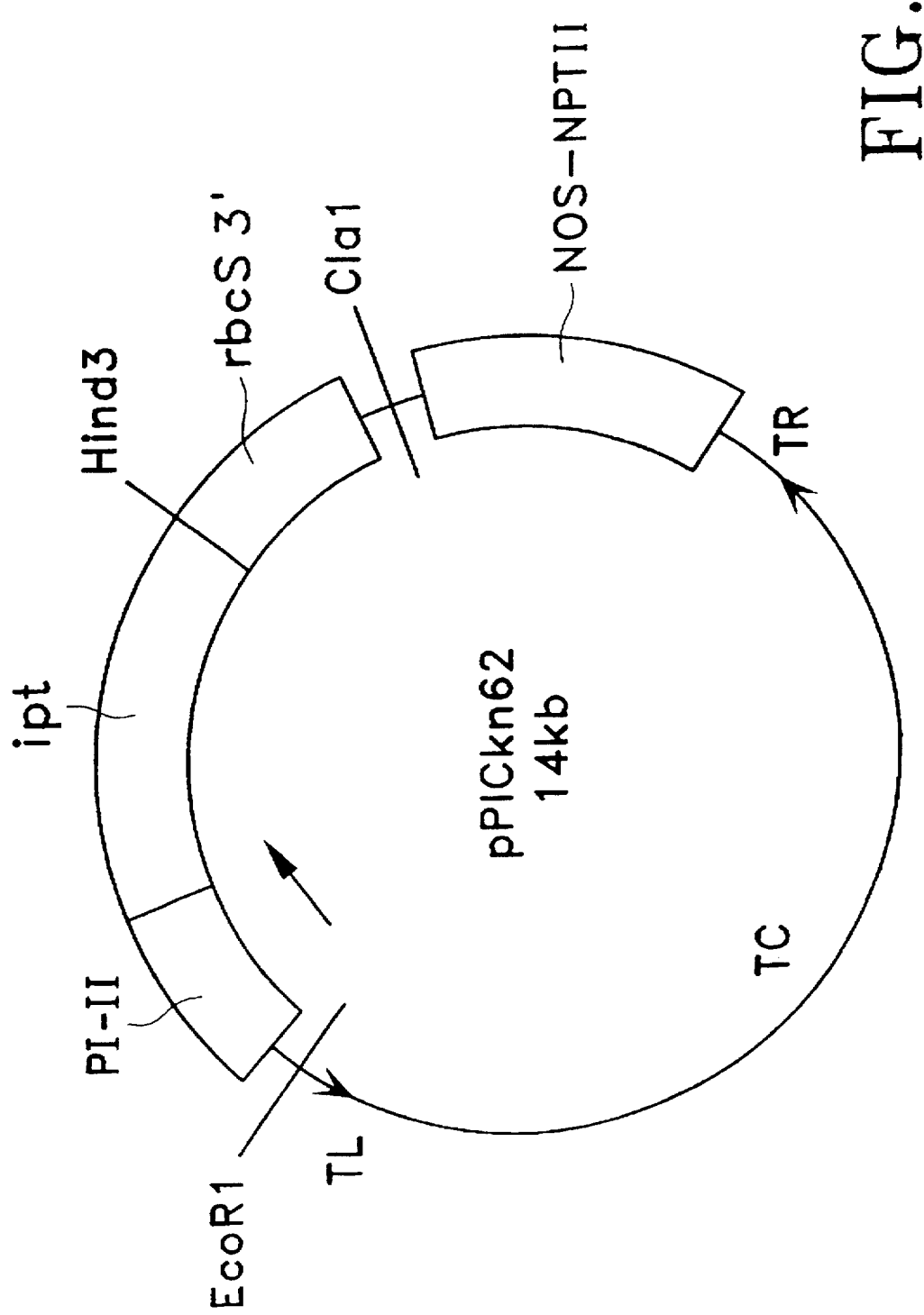

An EcoRI/HindIII PI-II-ipt fragment may be subcloned into any vector effective for introducing the gene construct into the plant. Vectors effective for this purpose are pBI221, pGMVNEO, pUC19, pCMC1100 and pDG208. In a preferred embodiment, the fragment was subcloned into a binary plant transformation vector and mobilized into *A. tumefaciens* for infection and transformation of leaf disks (FIG. 3B). Binary plant transformation vectors are known in the art, and selection of an effective vector is well within the level of skill in the art. Examples of useful vectors are pEND4K, pMON120, pMON200, pGA472, pKYOX4, pKYOX5, pBIN6, pBIN19, pAGS112, pAGS113, and pKYLX71. Preferred vectors are pKYOX4, pKYOX5, pBIN6, pBIN19, pAGS113 and pKYLX71, while particularly preferred is pKYLX71.

The ipt gene constructs were transferred to the plant genome by co-cultivation of *A. tumefaciens* with leaf disks. The leaf pieces may be preincubated on agar media for 1–2 days prior to infection with the bacteria to enhance transformation. After co-cultivation, leaf pieces were washed with media and plated on selective agar media containing kanamycin. Cefotaxime and carbenicillin are added to the wash media and selective agar media to kill all bacteria.

Kanamycin-resistant transformed shoots were regenerated, and shoots were transferred to fresh media and rooted in the presence of kanamycin sulfate. Seeds from the primary transformants were germinated on kanamycin-containing media and resistant progeny screened for wound inducible expression of the ipt gene.

Figure 3C:
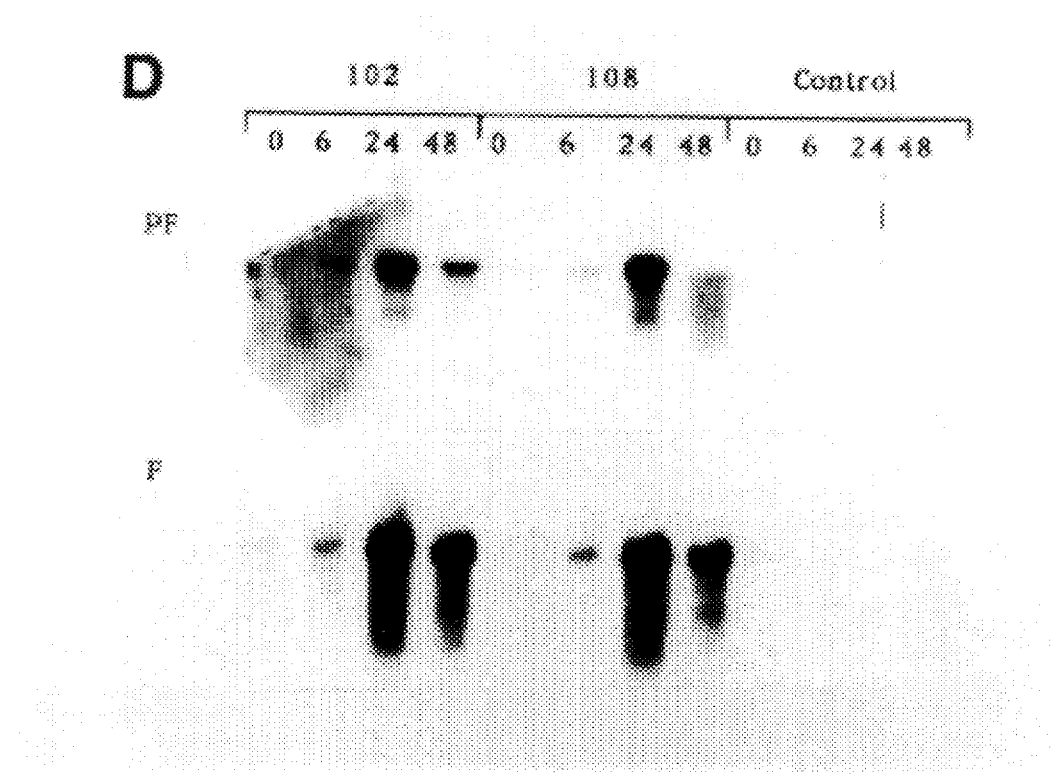

The ipt gene transcript levels in leaf disks excised from fully expanded leaves of preflowering and flowering PI-II-ipt increased approximately 25- to 35- fold in 24 hrs. About 50% of the transcripts were still detected after 48 hrs (FIG. 3C). At all time points analyzed, the ipt message levels in flowering plants were 2- to 5- fold higher than in preflowering plants.

The novel construct is useful for conferring enhanced insect resistance to a wide variety of plants. Agricultural crop plants are of particular importance because of their susceptibility to insect infestation and the need to reduce the amount of applications of chemical insecticides. Other plant types are contemplated, however, including fruit trees such as peach, plum, etc. as well as ornamental plants which are also susceptible to insects.

The following examples are intended only to further illustrate the invention and are not intended to limit the scope of the invention which is defined by the claims.

EXAMPLES

Example 1

A chimeric cytokinin gene was constructed by fusing the bacterial ipt gene to the 5' regulatory region of the potato PI-IIK gene as described supra. The 0.8 kb EcoRI/BamHI fragment was fused through its 5' untranslated region to the coding region of the ipt gene from pTiB6S3. An EcoRI/HindIII pPI-II-ipt fragment was subcloned into a binary plant transformation vector pKYLX71 and mobilized into A. tumefaciens strain EHA101 (pEHA101) for infection and transformation of Nicotiana plumbaginifolia (N. plumbaginifolia) leaf disks. A binary vector carrying a truncated ipt (t-ipt) gene without a functional promoter was used as a negative control for transformation experiments.

Example 2

Reconstructed ipt genes were transferred to the plant genome by cocultivation of A. tumefaciens with N. plumbaginifolia leaf disks. Leaves from 6- to 10-week old sterile plants were cut into approximately 4-mm×4-mm pieces and preincubated on agar media for 1–2 days prior to infection with the bacteria to enhance transformation. After a 24-hr cocultivation, the leaf pieces were washed with media containing Cefotaxime and carbenicillin (200 µg/ml, Sigma) and plated on selective agar media containing kanamycin (100 µg/ml) as well as the Cefotaxime and carbenicillin.

Ten kanamycin-resistant, independently transformed shoots were regenerated. Seeds from the primary transformants were germinated on kanamycin-containing media (100 µg/ml) and resistant progeny screened for wound inducible expression of the ipt gene. Three 1-in incisions were made on each half of a fully expanded leaf, and 24 hr later RNA was extracted and analyzed. Homozygous kanamycin-resistant R2 progeny were selected from R1 plants segregating 3:1 for kanamycin resistance.

Example 3

Fully expanded leaves on PI-II-ipt plants were used in leaf disk and whole leaf assays. Leaf disks 1.45 cm$^2$ were cut with a cork borer and placed in a 60×15 mm petri dish on filter paper wet with water or water plus the cytokinin zeatin at 10 and 20 µg/ml in 1 or 2% methanol, respectively (Sigma). Petioles of detached leaves were submerged in sealed vials containing water or water plus zeatin as above and placed in large petri dishes lined with filter paper. Surface areas of leaf disks and leaves were measured before and after insect feeding with a surface area meter (LI-COR, Inc., Lincoln, Nebr.). Data in FIGS. 4 and 5 was analyzed by analysis of variance and means were compared using the least significant difference test.

Manduca sexta (M. sexta) larvae (tobacco hornworms) were maintained on a meridic diet prior to feeding trials. For each experiment, a weighed neonate or a third-instar larvae was placed in a petri dish with either 5 leaf disks or a whole leaf. The larvae were allowed to feed for 48 or 72 hours.

Figure 4:
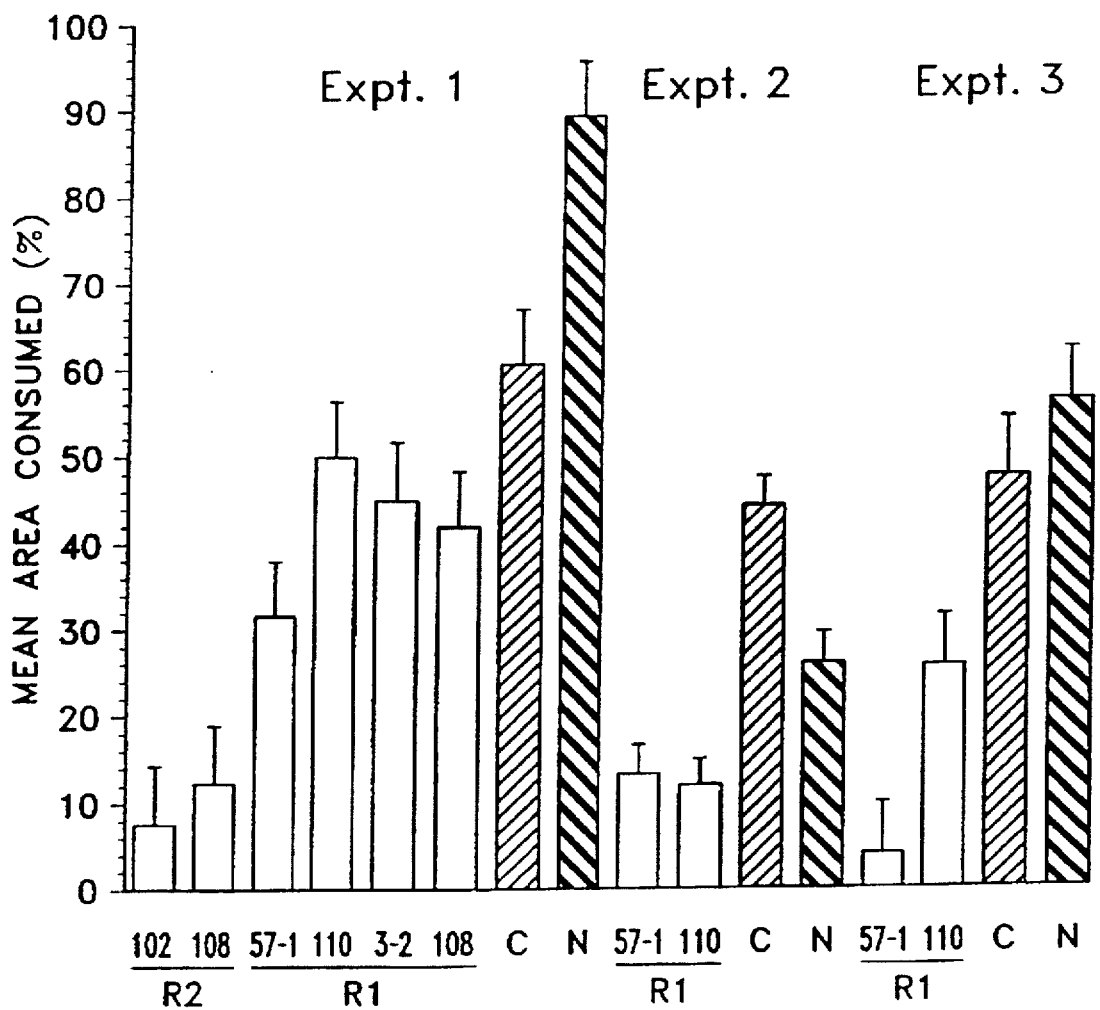
FIG. 4. Percent of mean leaf disk area consumed by larvae feeding on PI-II-ipt, transgenic control (C), and normal (N) plants in 48 hours. Disks were excised from homozygous R2 (102 and 108) and heterozygous RI (57-1, 110, 3-2 and 108) PI-II-ipt plants. Three plates per treatment were used in Expt. 1 and 5 plates in Expt. 2 and 3.

When whole plants were infested, a single neonate larvae was used per plant, and plants were wrapped during the last instar with cheesecloth to prevent escape. Larval weights were recorded weekly. Three to five plants per treatment were infested in 3 replicated experiments. Results are shown in FIG. 4. Larvae consumed only 8 and 13% of the leaf disks as measured by area when feeding on homozygous transformants 102 and 108, respectively (Experiment 1). In comparison, larvae fed disks excised from transgenic control and untransformed plants consumed 5–11 times more of the tissues. Insects feeding on disks from heterozygous R1 plants (57-1, 110, 3-2, 108) consumed approximately 20 to 50% less than those feeding on controls.

Figure 5A:
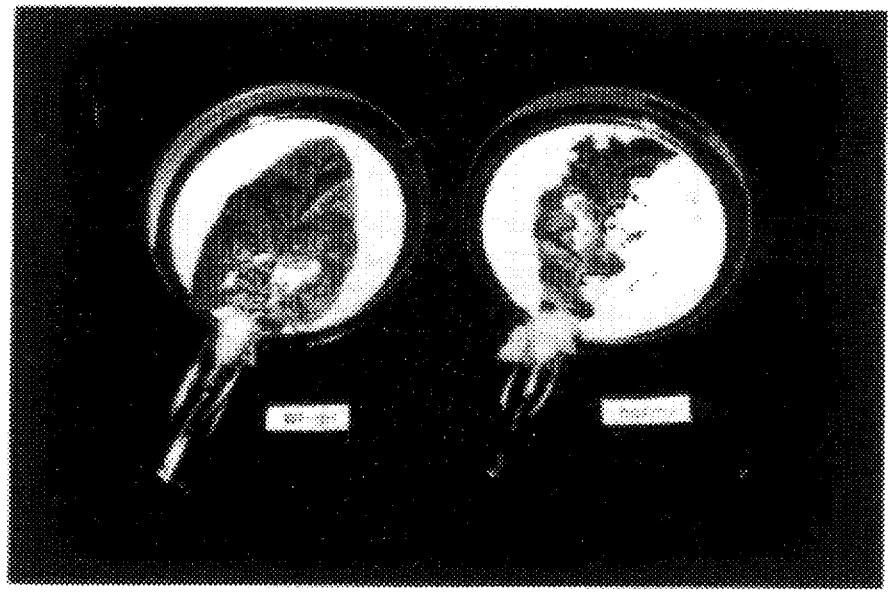
FIG. 5. Whole leaf assay for insect resistance. (A) Detached leaves from flowering, homozygous PI-II-ipt plant 102 (left) and transgenic control plant (right) 72 hours after infestation with third instar *M. sexta* larvae. (B) Mean leaf area consumed by larvae after 72 hours of feeding on flowering PI-II-ipt (102, 108), control (C) and normal (N) leaves. Ten leaves per treatment were used. (C) Mean weight gain of larvae feeding on the same leaves.
Figure 5B:
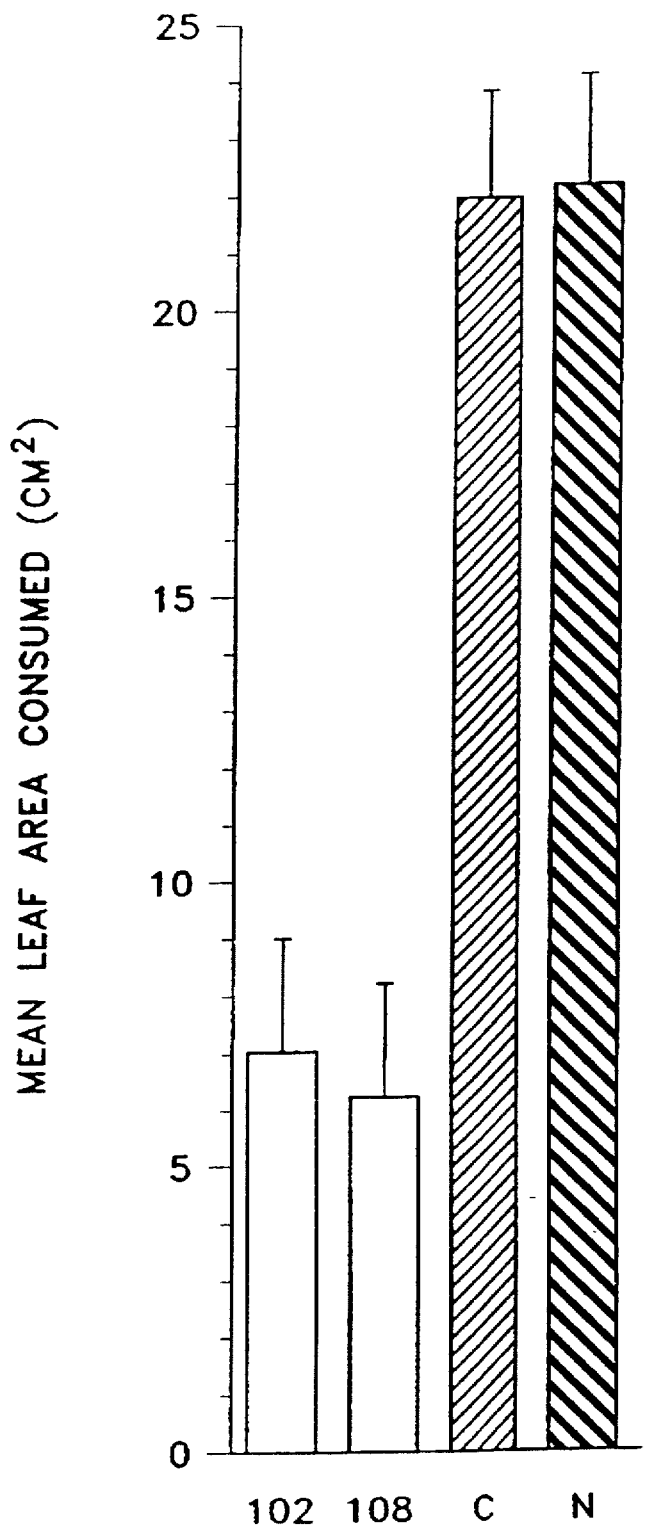
Figure 5C:
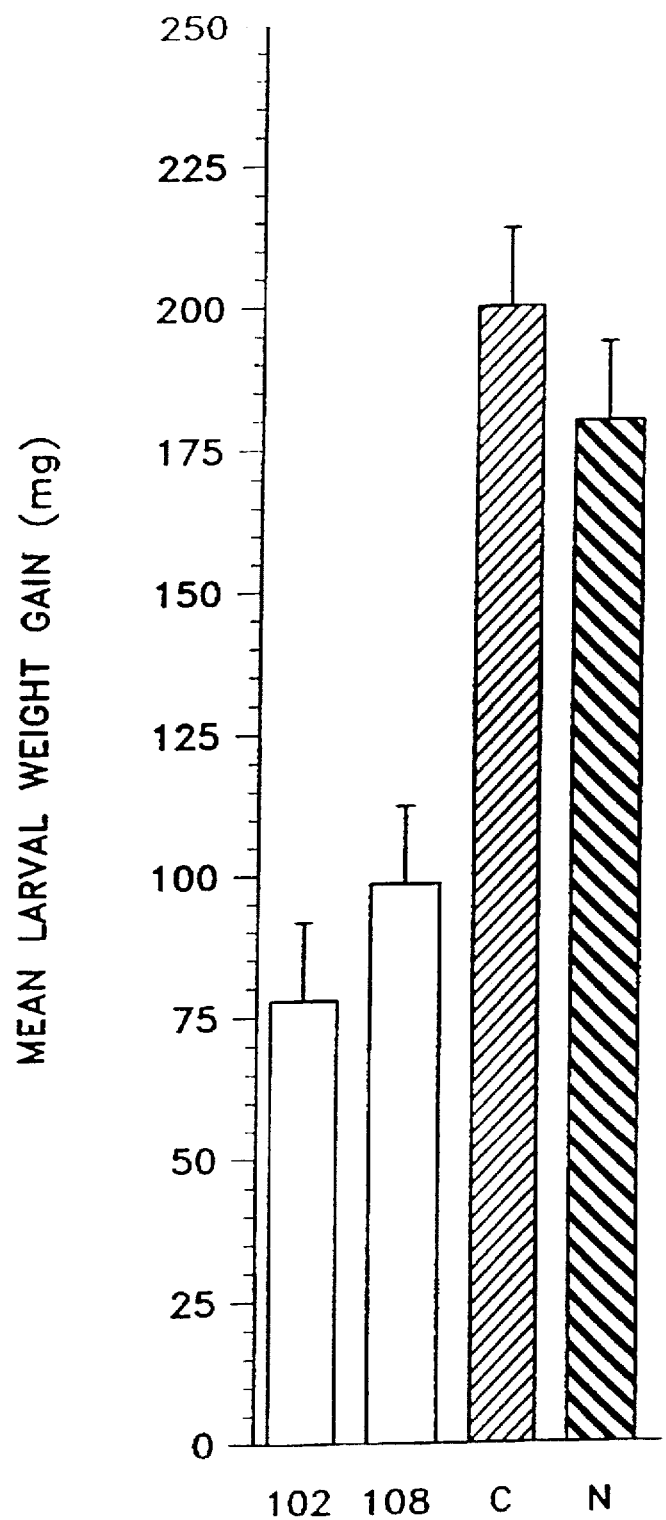

Two additional experiments with heterozygous plants 56-1 and 100 confirmed a significant decrease in leaf disk area consumption when compared to the controls. An overall reduction in all disks consumed by the larva in Experiments 2 and 3 corresponds to less feeding by neonates vs. third instar larvae used in Experiment 1. The specific leaf weight (g/cm$^2$) of the PI-II-ipt plants is reduced by about 40%, thereby increasing the significance of the observed enhanced resistance. Homozygous R2 progeny were further analyzed by an excised leaf assay (FIG. 5A). Third-instar tobacco hornworm larvae feeding on leaves from flowering (PI-II-ipt plants (102 and 108) consumed only about a third to a half of what was consumed by larvae feeding on control leaves (FIG. 5B; Table 1). Mean larval weight gain was reduced by approximately 30 to 60% compared to controls FIG. 5C; Table 1).

Figure 6:
FIG. 6. Enhanced resistance of PI-II-ipt plants (left) to *M. sexta* larvae as compared to transgenic control plants (right). After 19 days of feeding, the larvae consumed much less of the leaf material on flowering, homozygous 108 plants in comparison to control plants.

Resistance at the whole plant level was evaluated by infesting homozygous PI-II-ipt flowering plants with a single neonate hornworm larvae. Approximately 19 days later, the larvae pupated, however, the consumption of the PI-II-ipt plants was greatly reduced in comparison to the control plants (FIG. 6). In general, all the insects preferred the newly emerging and younger leaves, and only when these were exhausted did they feed on the older leaves. During the course of the experiment, weights of larvae feeding on PI-II-ipt or control plants did not differ significantly and all emerging adults appeared normal.

Myzus persicae (M. persicae), green peach aphid, nymphs were propagated in a rearing chamber for feeding experiments to evaluate the resistance of PI-II-ipt plants. A nymph less than 12 hr old was placed on a single leaf disk. After 8 days, it was determined whether the nymph was alive or dead, the stage of development (nymph or adult female) and whether or not the adult female had reproduced. Results are presented in Table 2.

After 8 days of feeding on disks from flowering PI-II-ipt plants (102 and 108), approximately 30 to 40% of the nymphs developed into adult females. Of those adults, 50 to 80% reproduced. On control and normal tissues, on the average, 74% of the nymphs reached adulthood, and 93% reproduced.

Feeding zeatin through petioles of leaves excised from PI-II-ipt plant prior to flower development, caused about a 40 to 60% reduction in mean area consumed by the tobacco hornworm larvae and a 30% reduction of mean larval weight gain as compared to normal controls (Table 1). Zeatin uptake by leaves from flowering PI-II-ipt plants boosted the level of insect resistance normally observed in these plants by up to 36% based on mean area consumed. A similar response to zeatin was not observed with any of the leaves from normal, untransformed plants. In control experiments with 1% methanol alone, no negative effects on the hornworm feeding were observed.

Placing leaf disks from PI-II-ipt or control and normal plants on filter paper wet with zeatin at 10 or 20 µg/ml delayed the development of the green peach aphid nymphs (Table 2). Of the surviving nymphs, most were immature and did not reproduce within the 8 day test. Nymphs feeding on control leaf disks placed in 1 or 2% methanol developed normally.

Table 1. Resistance of homozygous R2 PI-II-ipt plants (102, 108) to the tobacco hornworm larvae. Effects of zeatin (Z; 10 µg/ml) were determined by calculating the mean leaf area consumed and larval weight gain after 3 days of feeding. Each number represents an average of six replicates.

TABLE 1

| | Mean leaf area consumed (cm$^2$) | | | | Mean larval weight gain (g) | | | |
|---|---|---|---|---|---|---|---|---|
| | Preflowering | | Flowering | | Preflowering | | Flowering | |
| Plants | — | Z | — | Z | — | Z | — | Z |
| 102 | 25 | 9 | 18 | 5 | .23 | .22 | .17 | .10 |
| 108 | 24 | 14 | 14 | 11 | .25 | .23 | .23 | .17 |
| normal | 24 | 23 | 34 | 29 | .29 | .32 | .32 | .30 |

Table 2. Results of green peach aphid feedings on flowering homozygous R2 PI-II-ipt plants (102, 108) without and with exogenously supplied zeatin (Z; 10 µg/ml and 20 µg/ml). Presented are the percent of nymphs still alive and the percent of adult females (if any) that had reproduced at the end of the 8 day test. In tests without added zeatin, each number represents an average of four independent tests done in replicates of 10 disks per treatment. The zeatin results are averages of two independent tests with 5 disks per treatment.

TABLE 2

| | Percent alive Zeatin (µg) | | | Percent adult females with nymphs Zeatin (µg) | | |
|---|---|---|---|---|---|---|
| Plants | 0 | 10 | 20 | 0 | 10 | 20 |
| 102 | 40 | 10 | 10 | 53 | 0 | 0 |
| 108 | 32 | 50 | 10 | 83 | 50 | 0 |
| control | 67 | 20 | 20 | 89 | 0 | 0 |
| normal | 80 | 20 | 60 | 97 | 50 | 40 |

Experiment 4

The concentration of zeatin and N$^9$ substituted zeatin derivatives, major cytokinins produced in tissues transformed with the PI-II-ipt gene, were determined using analytical kits (De Danske Sukkerfabrikker, Copenhagen; IDETEK, Inc., San Bruno, Calif.). Plant tissues were extracted in 80% methanol overnight at −80° C. All extracts were purified on columns packed with anti-zeatinriboside antibodies, and eluted cytokinins were quantified by ELISA. To determine the percent recovery, control samples were spiked with 1000 to 2000 pmoles of zeatinriboside or zeatin (Sigma). For each plant, 3 to 4 samples were analyzed.

Levels of zeatin and zeatinriboside cytokinins were greatly elevated. On the average, zeatin and zeatinriboside concentrations increased to approximately 500 to 550 pmoles/g fresh tissue. This corresponds to a greater than 70-fold increase over endogenous cytokinin levels in control tissues. Cytokinin levels in detached leaves at the end of a 72-hr infestation were slightly lower (approximately 400 pmoles/g).

DISCUSSION

When the *M. sexta* larvae were fed leaf disks or whole leaves from flowering PI-II-ipt plants, they consumed significantly less of the plant material than larvae feeding on leaves from control plants (FIG. 4 and 5; Table 1). A corresponding decrease in larval weight gain was also observed. At the whole plant level, less PI-II-ipt leaves were consumed but no significant differences in larval weights were recorded (FIG. 6). It appears that sufficient feeding material is provided by younger leaves and the abundance of lateral buds released during reproductive stage of growth of the PI-II-ipt plants (Smigocki, unpublished). On normal plants, newly emerging and younger leaves have been reported to be preferred by these insects (Thornburg, supra). We find lower ipt transcript levels and cytokinin concentrations in younger leaves of transgenic PI-II-ipt plants (FIG. 3).

Green peach aphid feedings on leaf material from flowering PI-II-ipt plants delayed normal development of newly hatched nymphs into adult females by about 50% (Table 2). In addition, of the nymphs that reached maturity, fewer were able to reproduce as compared to controls. Enhanced resistance to the tobacco hornworm and green peach aphid is observed when PI-II-ipt plants are in the mid to late flowering stage of growth (Table 1).

Cytokinin levels were elevated by approximately 70-fold in comparison to controls. By boosting the endogenous cytokinin levels with exogenous applications of zeatin, enhanced resistance to the tobacco hornworm was induced in leaves from preflowering plants (Table 1). In addition, a higher degree of resistance was also observed when leaves from flowering PI-II-ipt plants were supplied with zeatin. This response to zeatin was not observed with leaves form normal, untransformed plants and may reflect problems associated with sufficient uptake, metabolism, or compartmentalization of exogenously supplied cytokinins necessary to retard hornworm feeding. The effects of exogenous zeatin applications on delaying the green peach aphid development were more dramatic in that most of the nymphs did not reach maturity. The green peach aphid tolerance to cytokinin effects appears to be lower than that of the tobacco hornworm and may be directly related to their much reduced overall body mass. Zeatin application results suggest that use of a stronger constitutive promoter to express the cytokinin gene would increase endogenous cytokinin concentrations to even higher levels than those in PI-II-ipt plants and result in better insect control. It has previously been reported that overexpression of the ipt gene with the 35S promoter from cauliflower mosaic virus increases zeatin levels up to several hundred fold in *N. plumbaginifolia* (Smigocki and Owens, 1989). However, the constitutive overproduction of cytokinin in plant cells inhibits regeneration of whole plants. Temporal and tissue specific expression allows for regeneration of plants and is preferred for expression of a foreign gene as for example in leaves upon insect feeding.

We claim:

1. A transgenic plant having enhanced resistance to insect feeding on plants, said plant comprising a gene construct comprising a wound inducible promoter region fused to a DNA sequence encoding the enzyme isopentenyl transferase.

2. The transgenic plant of claim 1, wherein the wound inducible promoter of said gene construct is derived from the potato proteinase inhibitor II gene.

3. The transgenic plant of claim 2, wherein said promoter is obtained from the 5' regulatory region of the potato proteinase IIK gene.

4. The transgenic plant of claim 1, wherein said DNA sequence is derived from *Agrobacterium tumefaciens*.

* * * * *